United States Patent
Werner et al.

(10) Patent No.: US 7,208,610 B2
(45) Date of Patent: Apr. 24, 2007

(54) PROCESS FOR ISOMERIZATION OF 2-HALOTHIOPHENE TO 3-HALOTHIOPHENE

(75) Inventors: Christian Werner, Hannover (DE); Andreas Kanschik-Conradsen, Garbsen (DE); Bernd Kellermeier, Lindhorst (DE); Hans-Jürgen Schmidt, Seelze-Lohnde (DE)

(73) Assignee: Honeywell International Inc., Morristown, NJ (US)

( * ) Notice: Subject to any disclaimer, the term of this patent is extended or adjusted under 35 U.S.C. 154(b) by 278 days.

(21) Appl. No.: 11/033,572

(22) Filed: Jan. 12, 2005

(65) Prior Publication Data

US 2006/0155133 A1    Jul. 13, 2006

(51) Int. Cl.
*C07D 333/28* (2006.01)
(52) U.S. Cl. ........................................................ 549/81
(58) Field of Classification Search .................... 549/81
See application file for complete search history.

(56) References Cited

U.S. PATENT DOCUMENTS

| | | | |
|---|---|---|---|
| 4,169,839 A | * | 10/1979 | Houbiers et al. ............. 549/81 |
| 4,604,470 A | | 8/1986 | Eichler et al. ................ 549/81 |
| 4,889,940 A | * | 12/1989 | Grosvenor et al. ........... 549/81 |
| 6,166,172 A | | 12/2000 | McCullough et al. ....... 528/380 |

OTHER PUBLICATIONS

Dettmeier U, et al "Preparation of Beta Halothiophenes by Isomerization of Alpha Halothiophenes on Zeolite Catalysts" Vo. 26, No. 5, 1987 pp. 468-469 XP002378685.

Brandsma, L. et al "A Large-Scale Procedure for the Preparation of 3-Bromothiophene from 2-Bromothiophene and Sodamide in Liquid Ammonia" dated 1990, pp. 1967-1700 XP 009065764.

* cited by examiner

*Primary Examiner*—Deborah C. Lambkin

(57) ABSTRACT

An improved process and catalyst system for the isomerization of halothiophenes. More particularly, an improved process for the isomerization of 2-halothiopehenes to 3-halothiophenes by reacting a 2-halothiophene with a catalyst and in the presence of a base. The addition of a base additive to the acidic zeolite catalyst allows the desired isomerization reaction to take place while suppressing side-reactions that result in the decomposition of thiophene rings. The catalyst lifetime is thus increased and the amount of catalyst needed for the reaction is reduced, lowering cost.

21 Claims, No Drawings

PROCESS FOR ISOMERIZATION OF 2-HALOTHIOPHENE TO 3-HALOTHIOPHENE

BACKGROUND OF THE INVENTION

1. Field of the invention

The present invention relates to an improved process and catalyst system for the isomerization of halothiophenes. More particularly, the invention pertains to an improved process for the isomerization of 2-halothiopehenes to 3-halothiophenes by reacting a 2-halothiophene with a zeolite catalyst and a base.

2. Description of the related art

Halogenated thiophenes are useful intermediates for the preparation of pharmaceuticals, plant protection agents, photovoltaic and conductive polymers, liquid crystal polymers and organic light-emitting diodes. As discussed in U.S. Pat. No. 4,604,470, which is incorporated herein by reference, 3-halothiophenes are particularly useful, yet typically are more difficult and expensive to produce compared to their 2-halothiophene counterparts. For example, while 2-chlorothiophene can be synthesized by chlorination of thiophene, 3-chlorothiophene is not accessible via this route. Other synthesis routes are therefore required for its preparation, for example, the reaction of 3-bromothiophene with CuCl. Further, 2-bromothiophene can be obtained, for example, by the bromination of thiophene in acetic acid, while 3-bromothiophene is prepared by the dehalogenation of 2,3,5-tribromothiophene with zinc dust in acetic acid.

One typical method used for the synthesis of 3-halothiophenes is the isomerization of its corresponding 2-halothiophene using a zeolite catalyst. However, such processes result in an inadequate product yield due to the decomposition of the thiophene ring during the isomerization process. In fact, nearly all of the methods currently known for the preparation of 3-chloro-, 3-bromo or 3-iodothiophene either require very expensive starting substances or give inadequate yields. Accordingly, previous known isomerization processes have suffered from low product yields, reduced catalyst lifetime, and hence, increased cost. Consequently, there is a need in the art for simpler and less expensive methods for the formation of 3-halothiophenes, particularly on an industrial scale.

It has now been found that 2-halothiophenes can be isomerized to 3-halothiophenes in good yields by the reaction of a 2-halothiophene in the presence of a zeolite catalyst and a base. It has been unexpectedly discovered that by the addition of a base as an additive to the acidic zeolite catalyst, not only will the desired isomerization reaction still take place, but the base additive suppresses the side-reaction that results in the decomposition of thiophene rings. This also has been found to increase the lifetime of the catalyst. Accordingly, the process allows for a reduction in the amount of catalyst needed for the synthesis reaction. It has been found the process of the invention is capable of producing a yield concentration of over 80% 3-halothiophene isomer without any major decomposition of the thiophene ring from the 2-halothiophene isomer reactant, and at a low cost.

SUMMARY OF THE INVENTION

The invention provides a process for isomerizing a 2-halothiophene to a 3-halothiophene comprising combining at least one 2-halothiophene with a zeolite catalyst and a base under conditions sufficient to isomerize said 2-halothiophene to the corresponding 3-halothiophene.

The invention also provides a process for isomerizing a 2-bromothiophene to a 3-bromothiophene comprising combining at least one 2-bromothiophene with a zeolite catalyst and a magnesium oxide base under conditions sufficient to isomerize said 2-bromothiophene to the corresponding 3-bromothiophene.

The invention further provides a process for isomerizing a 2-chlorothiophene to a 3-chlorothiophene comprising combining at least one 2-chlorothiophene with a zeolite catalyst and a magnesium oxide base under conditions sufficient to isomerize said 2-chlorothiophene to the corresponding 3-chlorothiophene.

DETAILED DESCRIPTION OF THE INVENTION

The process of the invention comprises the isomerization of a 2-halogenated thiophenes to a 3-halothiophene by the reaction of at least one 2-halothiophene with a zeolite catalyst and base. The reaction sequence proceeds as follows:

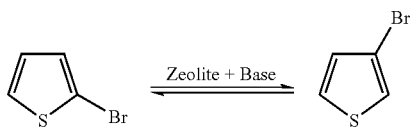

As described above, prior art methods utilizing only a zeolite are undesirable because the isomerization reaction typically stops at about 70%, and up to about 30% of the material is decomposed due to the acidic nature of the zeolite catalyst. Accordingly, an isolated yield of less than 40% can be realized without using a base. The addition of a base allows the isomerization reaction to take place while suppressing the decomposition of thiophene rings by the acidic zeolite catalyst.

The term "halogenated thiophenes" is intended to include all thiophenes containing one to three halogen atoms, for example, bromo-, chloro- and iodothiophenes, as well as dibromo-, tribromo-, dichloro-, trichloro-, diiodo and triiodo-thiophenes, bromo-chloro thiophenes. However, the process of the invention pertains particularly the isomerization of 2-halothiophenes to 3-halothiophenes.

In carrying out the process of the invention, a 2-halothiophene or a mixture of more than one 2-halothiophenes is combined with and reacted with both the zeolite catalyst and the base. As discussed herein, while zeolite catalysts, particularly acidic zeolites, are useful for the isomerization of halogenated thiophenes, they also cause undesirable side-reactions that result in the decomposition of thiophene rings. The base helps to suppress side-reactions and ring decomposition, but also is not too nucleophilic to attack the thiophene ring as well.

Zeolites are hydrated aluminosilicates of the alkaline and alkaline-earth metals. The term zeolite includes natural silicate zeolites, synthetic materials and phosphate minerals that have a zeolite like structure. More particularly, zeolites are framework silicates consisting of interlocking tetrahedrons of $SiO_4$ and $AlO_4$. The alumino-silicate structure is negatively charged and attracts the positive cations that reside within. Zeolites have large vacant spaces or cages in their structures that allow space for large cations such as sodium, potassium, barium and calcium and even relatively large molecules and cation groups such as water, ammonia, carbonate ions and nitrate ions. In some zeolites, the spaces are interconnected and form long wide channels of varying sizes depending on the mineral. These channels allow the easy movement of the resident ions and molecules into and out of the structure.

Zeolites have basically three different structural variations. There may be chain-like structures whose minerals form acicular or needle-like prismatic crystals, sheet-like structures where the crystals are flattened, platy or tabular with usually good basal cleavages, and framework structures where the crystals are more equant in dimensions. Suitable zeolites include both naturally occurring and synthetic zeolites. About forty-five natural minerals are recognized as zeolites, the most common being analcime, chabazite, clinoptilolite, erionite, ferrierite, heulandite, laumontite, mordenite, and phillipsite. More than 150 zeolites have been synthesized, with the most common being zeolites A, X, Y, and ZSM-5 (pentasil type, i.e. constructed of a five membered ring). More specifically, useful zeolites non-exclusively include those of the following types: analcime (hydrated sodium aluminum silicate), pollucite (hydrated cesium sodium aluminum silicate), wairakite (hydrated calcium sodium aluminum silicate), bellbergite (hydrated potassium barium strontium sodium aluminum silicate), bikitaite (hydrated lithium aluminum silicate), boggsite (hydrated calcium sodium aluminum silicate), brewsterite (hydrated strontium barium sodium calcium aluminum silicate), chabazite (hydrated calcium aluminum silicate) willhendersonite (hydrated potassium calcium aluminum silicate), cowlesite (hydrated calcium aluminum silicate), dachiardite (hydrated calcium sodium potassium aluminum silicate), edingtonite (hydrated barium calcium aluminum silicate), epistilbite (hydrated calcium aluminum silicate), erionite (hydrated sodium potassium calcium aluminum silicate), faujasite (hydrated sodium calcium magnesium aluminum silicate), ferrierite (hydrated sodium potassium magnesium calcium aluminum silicate), amicite (hydrated potassium sodium aluminum silicate), garronite (hydrated calcium aluminum silicate), gismondine (hydrated barium calcium aluminum silicate), gobbinsite (hydrated sodium potassium calcium aluminum silicate), gmelinite (hydrated sodium calcium aluminum silicate), gonnardite (hydrated sodium calcium aluminum silicate), goosecreekite (hydrated calcium aluminum silicate), harmotome (hydrated barium potassium aluminum silicate), phillipsite (hydrated potassium sodium calcium aluminum silicate), wellsite (hydrated barium calcium potassium aluminum silicate), clinoptilolite (hydrated sodium potassium calcium aluminum silicate), heulandite (hydrated sodium calcium aluminum silicate), laumontite (hydrated calcium aluminum silicate), levyne (hydrated calcium sodium potassium aluminum silicate), mazzite (hydrated potassium sodium magnesium calcium aluminum silicate), merlinoite (hydrated potassium sodium calcium barium aluminum silicate), montesommaite (hydrated potassium sodium aluminum silicate), mordenite (hydrated sodium potassium calcium aluminum silicate), mesolite (hydrated sodium calcium aluminum silicate), natrolite (hydrated sodium aluminum silicate), scolecite (hydrated calcium aluminum silicate), offretite (hydrated calcium potassium magnesium aluminum silicate), paranatrolite (hydrated sodium aluminum silicate), paulingite (hydrated potassium calcium sodium barium aluminum silicate), perlialite (hydrated potassium sodium calcium strontium aluminum silicate), barrerite (hydrated sodium potassium calcium aluminum silicate), stilbite (hydrated sodium calcium aluminum silicate), stellerite (hydrated calcium aluminum silicate), thomsonite (hydrated sodium calcium aluminum silicate), tschernichite (hydrated calcium aluminum silicate) and yugawaralite (hydrated calcium aluminum silicate).

Zeolites also have many "cousins" or minerals that have similar cage-like framework structures or have similar properties and/or are associated with zeolites, but are not technically zeolites. These include the phosphates kehoeite, pahasapaite and tiptopite, and the silicates hsianghualite, lovdarite, viseite, partheite, prehnite, roggianite, apophyllite, gyrolite, maricopaite, okenite, tacharanite and tobermorite. Natural and synthetic zeolites are used commercially because of their unique adsorption, ion-exchange, molecular sieve and catalytic properties. Also suitable are the zeolites discussed in U.S. Pat. No. 4,604,470, which is incorporated herein by reference in its entirety.

In the preferred embodiment of the invention, the zeolite comprises a zeolite of the pentasil, mordenite or faujasite type. The most preferred zeolite is a pentasil, H-ZSM-5. Zeolites are preferably employed in their acid form. These acid forms can be synthesized by known methods or may be naturally occurring. In the preferred embodiment of the invention, the zeolite is preferably combined with the 2-halothiophene or mixture of 2-halothiophenes at a zeolite:halothiophene weight ratio of from about 0.01:100 to about 100:100, more preferably from about 0.1:100 to about 10:100, and most preferably from about 1:100 to about 5:100.

The zeolite catalyst is preferably activated by calcination at temperatures of from about 300° C. to about 700° C., most preferably 500° C., before being used in the isomerization reaction according to the invention. This calcining process may optionally be carried out in the presence of steam, ammonia or mixtures thereof. Such procedures are well known in the art. The catalyst may also optionally be combined with a binder as described in U.S. Pat. No. 4,604,470.

Useful bases include amines, alkali imides, carbonates, basic silicates, basic aluminates, metal phosphates earth alkali oxides. In the preferred embodiment of the invention, the base is selected from the group consisting of chinoline, trimethylpyridine, sodium carbonate, potassium phthalimide and magnesium oxide. In the most preferred embodiment, the base comprises magnesium oxide. The base may be in the state of a liquid or solid, with a solid base being preferred. In the preferred embodiment of the invention, the base is preferably combined with the 2-halothiophene and zeolite catalyst at a base:zeolite weight ratio of from about 0.02:10 to about 100:10, more preferably from about 0.2:10 to about 10:10 and most preferably from about 2:10 to about 4:10.

The reaction of the invention may also optionally be conducted with one or more organic diluents. Organic diluents which may optionally be used non-exclusively include benzene, an alkylbenzene, a monoor poly-halogenated benzene or a mixture of these. If used, a preferred molar ratio of the diluent to the halothiophene is from about 0:1 to about 30:1, more preferably from about 0:1 to about 15:1, and most preferably from about 0:1 to about 1:5.

In a general process of the invention, a halogenated thiophene is brought in contact with a zeolite and a base for sufficient time at sufficient temperature. The catalyst is removed from the reaction mixture and the product is purified by a distillation process. If the reaction is to be carried out in the gas phase, the halogenated thiophene or thiophenes may be added from a metering device to a vaporization zone and then the gas formed thereby is passed through an externally heated reaction tube filled with the catalyst and the base. If the isomerization is carried out in the liquid phase, the thiophene or thiophenes are first preferably warmed and then passed in liquid form through a reaction tube filled with the catalyst and base.

In a continuous process, the isomerization reaction may be carried out in any suitable reactor, such as a fixed bed reactor or fluidized bed reactor. The throughput over the zeolite catalyst expressed as the Liquid Hourly Space Velocity (LHSV ($h^{-1}$)), is preferably from about 0.05 to about 10 $h^{-1}$, and more preferably from about 0.2 to about 5 $h^{-1}$.

The isomerization according to the invention is in general carried out by contacting the 2-halothiophene with the zeolite-base mixture at a preferred reaction temperature of from about 0° C. to about 400° C., more preferably from about 100° C. to about 250° C., and most preferably from about 140° C. to about 160° C. The preferred reaction pressures are from about 10 kPa to about 1000 kpa, more preferably from about 75 kPa to about 100 kPa, and most preferably the reaction is conducted at atmospheric pressure. In the preferred embodiment of the invention, the isomer mixture formed is separated by distillation using well known techniques. Any unreacted starting substances can then be recycled to the reactor. Once the reaction is complete, the result is a reaction mixture having an organic yield of at least about 90%, and as high as 99%, with a 3-halothiophene concentration of from about 1% to about 90% depending on the catalyst system and base, more preferably from about 80% to about 90% without any major decomposition. The process of the invention is an equilibrium process and accordingly the 3-halothiophene yield will not be above 90%. Any residual solids are filtered off and the reaction mixture is distilled over a packed column to give the desired 3-halothiophene product.

In a continuous operation, it is known that the catalyst activity may decreases and therefore should be reactivated or regenerated. This may be effected by passing a gas comprising oxygen, air, nitrogen-air, oxygen-air, oxygen-inert gas or air-inert gas over the deactivated catalyst at temperatures of from about 300° C. to about 650° C. The preferred gas for this purpose comprises a combination of nitrogen and air. Preferably, the temperature at which such a regeneration procedure is conducted should not exceed 650° C. at any point in the reactor.

The following non-limiting examples serve to illustrate the invention.

EXAMPLE 1

100 g of 2-bromothiophene, 3 g H-ZSM 5 and 1 g of solid magnesium oxide (MgO) are heated to 150° C. for 54 hours. The solid is filtered off. The reaction mixture is distilled over an 80 cm packed column; 95% of the organic material could be recovered. Gas chromatography (GC) analysis of the product showed 5% 2-bromothiophene and 89.7% 3-bromothiophene.

EXAMPLE 2

20 g of 2-bromothiophene, 1 g H-ZSM 5 and 1 g of solid MgO are heated to 150° C. for 30 hours. The solid is filtered off. 95% of the organic material could be recovered. GC analysis of the product showed 6.4% 2-bromothiophene and 87.3% 3-bromothiophene.

EXAMPLE 3

20 g of 2-bromothiophene, 0.2 g H-ZSM 5 and 0.2 g of solid MgO are heated to 150° C. for 30 hours. The solid is filtered off. 96% of the organic material could be recovered. GC analysis of the product showed 45.8% 2-bromothiophene and 51.1% 3-bromothiophene.

EXAMPLE 4

20 g of 2-bromothiophene, 0.02 g H-ZSM 5 and 0.02 g of solid MgO are heated to 150° C. for 30 hours. The solid is filtered off. 98% of the organic material could be recovered. GC analysis of the product showed 99.78% 2-bromothiophene and 0.19% 3-bromothiophene.

EXAMPLE 5

20 g of 2-bromothiophene, 1 g H-ZSM 5 and 0.1 g of solid MgO are heated to 150° C. for 30 hours. The solid is filtered off. 93% of the organic material could be recovered. GC analysis of the product showed 5.8% 2-bromothiophene and 87.4% 3-bromothiophene.

EXAMPLE 6

20 g of 2-bromothiophene, 0.2 g H-ZSM 5 and 0.02 g of solid MgO are heated to 150° C. for 30 hours. The solid is filtered off. 96% of the organic material could be recovered. GC analysis of the product showed 45.3% 2-bromothiophene and 51.4% 3-bromothiophene.

EXAMPLE 7

20 g of 2-bromothiophene, 0.02 g H-ZSM 5 and 0.002 g of solid MgO are heated to 150° C. for 30 hours. The solid is filtered off. 98% of the organic material could be recovered. GC analysis of the product showed 99.7% 2-bromothiophene and 0.21% 3-bromothiophene.

EXAMPLE 8

20 g of 2-bromothiophene, 1 g H-ZSM 5 and 0.1 g of solid MgO are heated to 150° C. for 30 hours. The solid is filtered off. 96% of the organic material could be recovered. GC analysis of the product showed 11.27% 2-bromothiophene and 78.36% 3-bromothiophene.

EXAMPLE 9

20 g of 2-bromothiophene, 0.2 g H-ZSM 5 and 0.004 g of solid MgO are heated to 150° C. for 30 hours. The solid is filtered off. 97% of the organic material could be recovered. GC analysis of the product showed 48.98% 2-bromothiophene and 47.98% 3-bromothiophene.

EXAMPLE 10

20 g of 2-bromothiophene, 0.6 g H-ZSM 5 and 0.2 g of solid $Na_2CO_3$ are heated to 150° C. for 30 hours. The solid is filtered off. 92% of the organic material could be recovered. GC analysis of the product showed 10.94% 2-bromothiophene and 83.02% 3-bromothiophene.

EXAMPLE 11

20 g of 2-bromothiophene, 0.6 g H-ZSM 5 and 0.2 g of solid NaHCO$_3$ are heated to 150° C. for 30 hours. The solid is filtered off. 93% of the organic material could be recovered. GC analysis of the product showed 17.35% 2-bromothiophene and 77.44% 3-bromothiophene.

EXAMPLE 12

20 g of 2-bromothiophene, 0.6 g H-ZSM 5 and 0.2 g of solid potassium phthalimide are heated to 150° C. for 30 hours. The solid is filtered off. 96% of the organic material could be recovered. GC analysis of the product showed 87.19% 2-bromothiophene and 11.7% 3-bromothiophene.

EXAMPLE 13

20 g of 2-bromothiophene, 0.6 g H-ZSM 5 and 0.6 g of liquid chinoline are heated to 150° C. for 30 hours. The solid is filtered off. 98% of the organic material could be recovered. GC analysis of the product showed 99% 2-bromothiophene and 1% 3-bromothiophene.

EXAMPLE 14 (COMPARATIVE)

20 g of 2-bromothiophene, 0.6 g H-ZSM 5 are heated to 150° C. for 30 hours. Hydrogen Bromide (HBr) development is observed. The solid is filtered off. 65% of the organic material could be recovered. GC analysis of the product showed 16.66% 2-bromothiophene and 76.33% 3-bromothiophene.

While the present invention has been particularly shown and described with reference to preferred embodiments, it will be readily appreciated by those of ordinary skill in the art that various changes and modifications may be made without departing from the spirit and scope of the invention. It is intended that the claims be interpreted to cover the disclosed embodiment, those alternatives which have been discussed above and all equivalents thereto.

What is claimed is:

1. A process for isomerizing a 2-halothiophene to a 3-halothiophene comprising combining at least one 2-halothiophene with a zeolite catalyst and a base under conditions sufficient to isomerize said 2-halothiophene to the corresponding 3-halothiophene.

2. The process of claim 1 wherein said 2-halothiophene comprises a thiophene having from one to three halogen atoms.

3. The process of claim 1 wherein said 2-halothiophene comprises 2-bromothiophene and said 3-halothiophene comprises 3-bromothiophene.

4. The process of claim 1 wherein said 2-halothiophene comprises 2-chlorothiophene and said 3-halothiophene comprises 3-chlorothiophene.

5. The process of claim 1 comprising reacting a plurality of 2-halothiophenes with said zeolite catalyst and said base under conditions sufficient to isomerize each of said 2-halothiophene to the corresponding 3-halothiophene.

6. The process of claim 1 wherein said zeolite is selected from the group consisting of pentasil, mordenite and faujasite zeolites.

7. The process of claim 1 wherein said zeolite is selected from the group consisting of pentasil zeolites.

8. The process of claim 1 wherein said base is selected from the group consisting of amines, alkali imides, carbonates, basic silicates, basic aluminates, metal phosphates and earth alkali oxides.

9. The process of claim 1 wherein said base is selected from the group consisting of chinoline, trimethylpyridine, sodium carbonate, potassium phthalimide and magnesium oxide.

10. The process of claim 1 wherein said base comprises magnesium oxide.

11. The process of claim 1 wherein said zeolite catalyst is combined with the at least one 2-halothiophene at a zeolite:halothiophene weight ratio of from about 0.01:100 to about 100:100.

12. The process of claim 1 wherein said zeolite catalyst is combined with the at least one 2-halothiophene at a zeolite:halothiophene weight ratio of from about 0.1:100 to about 10:100.

13. The process of claim 1 wherein said zeolite catalyst is combined with the at least one 2-halothiophene at a zeolite:halothiophene weight ratio of from about 1:100 to about 5:100.

14. The process of claim 1 wherein the base is combined with the at least one 2-halothiophene and zeolite catalyst at a base:zeolite weight ratio of from about 0.02:10 to about 100:10.

15. The process of claim 1 wherein the base is combined with the at least one 2-halothiophene and zeolite catalyst at a base:zeolite weight ratio of from about 0.2:10 to about 10:10.

16. The process of claim 1 wherein the base is combined with the at least one 2-halothiophene and zeolite catalyst at a base:zeolite weight ratio of from about 2:10 to about 4:10.

17. The process of claim 1 wherein said reacting is conducted at a temperautre of from about 0° C. to about 400° C.

18. The process of claim 1 wherein the reacting is conducted at a pressure of from about 10 kPa to about 1000 kPa.

19. The process of claim 1 wherein the reacting is conducted at about atmospheric pressure.

20. A process for isomerizing a 2-bromothiophene to a 3-bromothiophene comprising combining at least one 2-bromothiophene with a zeolite catalyst and a magnesium oxide base under conditions sufficient to isomerize said 2-bromothiophene to the corresponding 3-bromothiophene.

21. A process for isomerizing a 2-chlorothiophene to a 3-chlorothiophene comprising combining at least one 2-chlorothiophene with a zeolite catalyst and a magnesium oxide base under conditions sufficient to isomerize said 2-chlorothiophene to the corresponding 3-chlorothiophene.

* * * * *